US012569182B2

(12) United States Patent
Bear et al.

(10) Patent No.: US 12,569,182 B2
(45) Date of Patent: Mar. 10, 2026

(54) METHOD FOR SELECTING ELECTROPHYSIOLOGICAL DESCRIPTORS

(71) Applicants: UNIVERSITE DE BORDEAUX, Bordeaux (FR); CENTRE HOSPITALIER UNIVERSITAIRE DE BORDEAUX, Talence (FR); FONDATION BORDEAUX UNIVERSITE, Bordeaux (FR)

(72) Inventors: Laura Bear, Talence (FR); Olivier Bernus, Lacanau de Mois (FR); Rémi Dubois, Merignac (FR); Michel Haissaguerre, Talence (FR); Nolwenn Tan, Libourne (FR)

(73) Assignees: UNIVERSITE DE BORDEAUX, Bordeaux (FR); CENTRE HOSPITALIER UNIVERSITAIRE DE BORDEAUX, Talence (FR); FONDATION BORDEAUX UNIVERSITE, Bordeaux (FR)

( * ) Notice: Subject to any disclaimer, the term of this patent is extended or adjusted under 35 U.S.C. 154(b) by 284 days.

(21) Appl. No.: 18/550,630

(22) PCT Filed: Mar. 25, 2022

(86) PCT No.: PCT/EP2022/057991
§ 371 (c)(1),
(2) Date: Sep. 14, 2023

(87) PCT Pub. No.: WO2022/200602
PCT Pub. Date: Sep. 29, 2022

(65) Prior Publication Data
US 2024/0148306 A1 May 9, 2024

(30) Foreign Application Priority Data

Mar. 25, 2021 (FR) ...................................... 2103047

(51) Int. Cl.
*G16H 20/30* (2018.01)
*A61B 5/349* (2021.01)
(Continued)

(52) U.S. Cl.
CPC ............. *A61B 5/349* (2021.01); *G16H 20/30* (2018.01); *G16H 50/70* (2018.01); *A61B 5/282* (2021.01)

(58) Field of Classification Search
CPC ....... A61B 5/349; A61B 5/0806; A61B 5/726; A61B 5/7285; A61B 5/304; A61B 5/308;
(Continued)

(56) References Cited

U.S. PATENT DOCUMENTS

2010/0049069 A1* 2/2010 Tarassenko ............ A61B 5/369
600/512

FOREIGN PATENT DOCUMENTS

WO WO 99/55228 A1 11/1999

OTHER PUBLICATIONS

International Search Report as issued in International Patent Application No. PCT/EP2022/057991, dated Jul. 7, 2022.
(Continued)

*Primary Examiner* — Ankit D Tejani
*Assistant Examiner* — Joshua Brendon Solomon
(74) *Attorney, Agent, or Firm* — Pillsbury Winthrop Shaw Pittman LLP

(57) ABSTRACT

A method for selecting a subset of electrophysiological descriptors from a set of electrophysiological descriptors, includes procedures for estimating values of a set of electrophysiological descriptors and selecting a subset of descriptors as a function notably of quantifications of proximity factors.

16 Claims, 3 Drawing Sheets

(51) Int. Cl.
　　G16H 50/70 　　　　(2018.01)
　　*A61B 5/282* 　　　　(2021.01)

(58) Field of Classification Search
　　CPC ................ A61B 5/6805; A61B 5/7267; A61B
　　　　　　　　2562/046; G16H 20/30; G16H 50/70
　　See application file for complete search history.

(56) 　　　　　　　References Cited

OTHER PUBLICATIONS

Magrupov, T., et al. "A Technique for Classifying the ECG Signal into Various Possible States of the Cardiovascular System," 2020 IEEE International Conference On Electrical Engineering and Photonics (Eexpolytech), Oct. 2020, XP033850052, pp. 127-131.

Anonymous: "Electrocardiography—Wikipedia," Mar. 2021, XP055871740, Retrieved from the Internet: URL:https://fr.wikipedia. org/w/index.php?title=Electrocardiographie&oldid=180729 180, [retrieved on Dec. 10, 2021], 29 pages.

Anonymous: "1.3.5.11. Measures of Skewness and Kurtosis," Feb. 2020, XP055871778, Retrieved from the Internet: URL:https://web. archive.org/web/20200226182752/https://www.itl.nist.gov/div898/ handbook/eda/section3/eda35b.htm, [retrieved on Dec. 10, 2021], 4 pages.

Anonymous: "Wavelet transform modulus maxima method—Wikipedia," Mar. 2021, XP055871785, Retrieved from the Internet: URL:https://en.wikipedia.org/w/index.php?title=Wavelet_transform_ modulus_maxima_method&oldid=1012638658, [retrieved on Dec. 10, 2021], 3 pages.

\* cited by examiner

METHOD FOR SELECTING ELECTROPHYSIOLOGICAL DESCRIPTORS

CROSS-REFERENCE TO RELATED APPLICATIONS

This application is the U.S. National Stage of PCT/EP2022/057991, filed Mar. 25, 2022, which in turn claims priority to French patent application number 2103047 filed Mar. 25, 2021. The content of these applications are incorporated herein by reference in their entireties.

FIELD OF THE INVENTION

The field of the invention relates to methods and devices for selecting a set of electrophysiological descriptors linked to an individual's cardiac activity. More particularly, the field of the invention relates to methods implemented by means of surface electrodes recording signals used to detect a representative cardiac electrical activity.

PRIOR ART

Currently, there are means for analyzing signals from surface electrodes in order to identify an electrical activity of the myocardium. This analysis makes it possible to prevent certain cardiac pathologies by identifying singular electrical activities within the myocardium.

These means, even though very reliable, only focus on a limited number of cardiac activity indicators derived from the analysis of cardiac electrical signals. For example, the duration of the QRS is frequently used, designating the duration of ventricular depolarization, as an indicator of cardiac pathologies. This measurement is a very good indicator for detecting certain singular activities of the heart, but this measurement alone is only an outline of certain cardiac characteristics. For example, it is possible for a patient with a given pathology that the measurement of QRS duration may be representative of an electrophysiological singularity. However, this measurement may prove to be insufficient to characterize certain electrophysiological activities of an individual, notably an electrophysiological activity that can be used or corroborated with other variables to anticipate a cardiac risk.

Thus, by focusing on few parameters, it is common not to detect characteristic electrophysiological activities.

Currently known methods have the drawback, by focusing on a very limited number of indicators, of offering only a very limited view of a patient's cardiac activity.

To date, existing solutions aim to confirm or detect the presence of a singular electrical activity. However, this activity usually remains at a low level or drowned in noise or even masked by a larger electrical pattern such as a QRS complex. No solution makes it possible, from a plurality of surface electrodes, to determine the characteristics of a source of a singular electrical activity or even to know, from a wide range of electrophysiological variables of a patient, which are likely to form a corpus of singularities that can be used for medical purposes or to prevent a cardiac risk.

The invention therefore aims to propose a method for selecting parameters for measuring the cardiac activity of a patient that addresses the aforementioned drawbacks.

SUMMARY OF THE INVENTION

According to one aspect, the invention relates to a method for selecting a subset of first electrophysiological descriptors characteristic of a characteristic cardiac electrical activity from a set of first predefined descriptors. Each first electrophysiological descriptor is associated with at least one channel, one signal type, one signal marker and one statistical modality for calculation. The method comprises a recording of a plurality of electrical activities defining said channels and comprises:

Estimation, for a first set of patients not having a predefined condition, of values of each descriptor of the set of predefined descriptors;

Estimation, for a second set of patients having the predefined condition, of values of each descriptor of the set of predefined descriptors;

Generation of a first vector characteristic of the condition of each patient of the first and second sets of patients in which each component corresponds to a condition relative to the predefined condition;

Generation of a descriptor vector for each descriptor in a metric space in which each component corresponds to the value of the descriptor for each patient;

First quantification for each descriptor of a first proximity factor between the values of the components of the first characteristic vector and the values of the components of the descriptor vector;

First selection and inclusion in the subset of at least one descriptor having optimal quantified proximity factor values;

Second quantification:

of a second proximity factor between the values of the components of each descriptor not selected during the first selection step and the values of the components of the descriptor vector(s) selected during the first selection step; and a third proximity factor between the values of the components of each descriptor not selected during the first selection step and the characteristic vector component values;

Second selection and inclusion in the subset of at least one new descriptor as a function of the value of the second proximity factor and the value of the third proximity factor quantified during the step of second quantification.

One advantage of the invention is to propose a method for selecting a subset of different electrophysiological descriptors to characterize a cardiac activity. The selection method according to the invention makes it possible to select a subset of electrophysiological descriptors that is relevant to discriminate between two different populations, from a set of physiological descriptors. Thus, it is possible to select from a large number of descriptors that take into account different signal types, different signal markers and various statistical modalities for calculation, a relevant subset of descriptors. Furthermore, since the method according to the invention comprises a second selection step taking into account the third proximity factor, a set of electrophysiological descriptors that are not redundant with each other is obtained to characterize said cardiac activity. The selection method according to the invention therefore makes it possible to obtain an effective and non-redundant subset for the discrimination of two populations.

According to one embodiment, at least one first descriptor of the subset is associated with a statistical modality different from that of another first descriptor of the subset and a signal marker different from that of the other first descriptor. This provision makes it possible to obtain a sub-assembly which comprises several descriptors bearing different physiological information from each other.

The different steps of the method according to the invention may be implemented by calculation means such as calculators. The latter may be those of an electronic board of dedicated equipment or those of a remote computer or data server.

According to one embodiment, the steps of second quantification and second selection are reproduced from the descriptors not selected previously until a predefined number of selected descriptors is obtained. This provision makes it possible to build the subset of descriptors iteratively by each time taking descriptors bearing information different from those borne by the descriptors already selected.

According to one embodiment, the quantification of the first proximity factor and/or the second proximity factor, and/or the third proximity factor is a correlation calculation. A correlation calculation is an effective way of estimating the proximity between two vectors. For example, the correlation is made between vectors defined in the metric space.

According to one embodiment, the step of second quantification comprises a step of projection, in a first plane orthogonal to the descriptor vector(s) associated with the last selected descriptors, of each unselected descriptor vector and the characteristic vector; in that the quantification of the third proximity factor and performed from the projected vector projection components; and in that the second selection is made as a function of the third proximity factor only. According to this provision, the projection in the plane orthogonal to the selected descriptor vector makes it possible to remove the descriptor vectors very close to the selected descriptor vector. This provision therefore makes it possible to select one or more descriptor vectors that bear different information.

According to another embodiment, the step of second quantification may be implemented by another operator than the projection. An operator making it possible to define a distance in the metric space of vectors may be used to calculate one of the proximity factors, notably the first proximity factor, the second proximity factor, and the third proximity factor. According to one embodiment, different operators may be configured so as to calculate the different proximity factors. It is understood in the present invention that a proximity factor is comprised with respect to a distance defined in the metric space. Thus, certain distances may have advantageous properties depending on the proximity factor that is measured. Certain operators favor certain dimensions of vectors during quantification, others make it possible to favor a measurement of approximation or proximity of vectors with each other, while others favor the distance, the orthogonalization or the difference of vectors between them. Thus, the projection of two vectors makes it possible to obtain a quantification of a proximity factor in a subspace, however other methods, such as calculating the quadratic error between two vectors, may be used to define a distance for the purpose of quantifying a proximity factor.

According to one embodiment, the predefined number of selected descriptors is determined by testing the effectiveness of a set of first "n" selected descriptors to characterize a given electrical activity, "n" corresponding to the number of descriptors taken from the selected descriptors, starting from the first to the nth selected descriptor, and incrementing the value of n by steps of 1. This provision makes it possible to calibrate the size of the subset of descriptors to have the subset with the greatest effectiveness.

According to one embodiment, the set comprises at least one second geographical descriptor associated with several channels and several geographical groups, each geographical group being formed by a central channel and the at least four channels close to the central channel, the value of the electrophysiological descriptor being determined:

By comparing the value, for each geographical group, of the measurement of each channel according to the signal type and the signal marker selected with at least one geographical threshold value specific to said electrophysiological descriptor and said channel; and By counting the number of geographical groups for which the value of at least three channels exceeds its own geographical threshold value.

According to this provision, in addition to the first electrophysiological descriptors, second descriptors are used which take into account geographical groups. The addition of this other type of descriptors makes it possible to take into account the concentration of singular measured values and enriches the subset of selected descriptors.

According to one embodiment, for each first descriptor, the at least one channel is derived from a predefined area on the body of the patient is chosen between:

An upper right area of the torso;

An upper left area of the torso;

A lower right area of the torso;

A lower left area of the torso; and

The entire torso of the patient.

This provision makes it possible to have descriptors that take into account the geographical location on the patient's body of the measurements taken. Thus, there is a variety of descriptors that take into account several types of information.

According to one embodiment, for each descriptor, the signal type analyzed is chosen between:

A unipolar signal taken between an electrode of the chosen body area and a reference electrode;

A vertical bipolar signal taken between two electrodes of the given area, one of the two electrodes being offset along a vertical line with respect to the other electrode;

A horizontal bipolar signal taken between two electrodes of the given area, one of the two electrodes being offset along a horizontal line with respect to the other electrode; and A Laplacian signal estimated by subtracting from the potential of a central electrode the average tension of the eight electrodes directly adjacent to said central electrode.

This provision makes it possible to take into account several types of signals and therefore to have descriptors that take into account several types of signal measurement. Thus, the descriptors take into account several types of information and report more faithfully on the condition of said patient.

According to one embodiment, the reference electrode is an electrode arranged on the surface of an upper limb or lower limb of the patient. This provision makes it possible to measure a reference potential.

According to one embodiment, a plurality of reference electrodes is arranged on the surface of the patient's lower or upper limb(s). This provision makes it possible to obtain a reference potential with high precision.

According to one embodiment, for at least one descriptor, the signal marker is the voltage measurement of an averaged signal. The averaging of the signal makes it possible to obtain a stable measurement of said voltage.

According to one embodiment, for at least one descriptor, the signal marker is the measurement, on the averaged and filtered signal between 40 and 250 Hertz, of the duration of depolarization of the ventricles or fragmentation of the signal during depolarization of the ventricles. The duration of ventricular depolarization is a very representative measurement of cardiac activity.

According to one embodiment, for at least one descriptor, the signal marker is the measurement on the discrete wavelet decomposition of the signal:

Of the energy of the sum of the wavelets;
Of the Kurtosis;
Of the Fisher asymmetry coefficient; or
Of the number of local minima.

This provision enables different types of signals all bearing different information enriching the selected subset to be taken into account.

According to one embodiment, for at least one descriptor, the signal marker is the measurement on the continuous wavelet decomposition of the signal of the number of local maxima chains. This measurement is a measurement that makes it possible to report a singular cardiac activity.

According to one embodiment, for at least one descriptor, the signal marker is the measurement on the wavelet taken between 256 and 512 Hertz of the signal:

Of the Kurtosis; or
Of the number of areas with reduced amplitudes.

These measurements make it possible to report measurements on the curve such as the flattening thereof.

According to one embodiment, for at least one descriptor, the signal marker is the measurement on the wavelet taken between 128 and 256 Hertz of the signal:

Of the Kurtosis;
Of the number of areas of reduced amplitude; or
Of the RMS (Root Mean Square).

These measurements make it possible to report measurements on the curve such as the flattening thereof.

According to one embodiment, for at least one descriptor, the signal marker is the measurement on the wavelet taken between 64 and 128 Hertz of the RMS (Root Mean Square). This measurement is used to report the patient's cardiac activity.

According to one embodiment, for each first descriptor, the statistical modality is chosen from:

The fifth percentile minimum of the measured values of the signal on each electrode in the predefined area;
The ninety fifth percentile maximum of the measured values of the signal on each electrode of the predefined area;
The average of the measured values of the signal on each electrode of the predefined area;
The standard deviation of the measured values of the signal on each electrode of the predefined area;
The median of the measured values of the signal on each electrode of the predefined area; and
The interquartile of the measured values of the signal on each electrode of the predefined area.

This provision makes it possible to select a statistical modality that makes it possible to process the multiple measurements made while choosing the statistical modality that is relevant, according to whether it is wished to analyze maxima or minima for example. These modalities also make it possible to avoid extreme aberrant measurements.

According to one embodiment, the method of the present invention may be succeeded by a method for generating an electrophysiological parameter to characterize a cardiac activity.

Such a step may be implemented by a method for generating an electrophysiological parameter which comprises:

selection of a subset of electrophysiological descriptors from a set of predefined electrophysiological descriptors according to an input parameter defining a measurement context, each electrophysiological descriptor of the subset being associated with at least one channel, a signal type, a signal marker and a statistical modality for calculation;
arrangement of a plurality of surface electrodes on a patient's body;
recording of a plurality of cardiac electrical activities defining said channels, each channel being obtained by the recordings of at least two electrodes;
estimation of all the electrophysiological descriptors of the subset, each electrophysiological descriptor being calculated from the statistical modality that is applied to the signal marker of the acquired signal according to the signal type on a selected channel associated with said electrophysiological descriptor;
comparison of the value of all the electrophysiological descriptors with at least one threshold value specific to all the electrophysiological descriptors, said at least one threshold value being defined by a statistical distribution of said descriptors of a set of healthy patients;
calculation of a score defining an electrophysiological parameter as a function of the exceeding of at least one threshold value defined by the statistical distribution.

According to one aspect, the invention relates to a device or a system comprising means for implementing the method of the invention. The means may comprise calculators, memories, electronic boards, electrodes and electrode holders. The device or the system of the invention may comprise computers or servers when calculation resources are required. The invention is hereafter described such that the described characteristics may relate to the method of the invention or to the device or the system of the invention.

The invention also relates to a device for selecting a subset of electrophysiological descriptors. The device according to the invention is capable of implementing the method mentioned previously. Subsequently, the elements described in this description will be applicable both to the method according to the invention and to the device according to the invention.

The invention also relates to a device for selecting a subset of electrophysiological descriptors which comprises:

a plurality of surface electrodes configured to be deposited on a patient's body and to measure an electrical potential of the surface of the patient's body, each surface electrode defining a channel;
a means of measuring the signal of each channel;
a calculation means configured to:
i. Estimate for a first set of patients not having a predefined condition, values of each electrophysiological descriptor of a set of first predefined descriptors, each first descriptor being associated with at least one channel, a signal type, a signal marker and a statistical modality for calculation; at least one first descriptor of the subset being associated with a statistical modality different from that of another first descriptor of the subset and a signal marker different from that of the other first descriptor;
ii. Estimate for a second set of patients with the predefined condition, values of each descriptor of the set of predefined descriptors;
iii. Generate a first vector characteristic of the condition of each patient of the first and second sets of patients in which each component corresponds to a condition relative to the predefined condition;

iv. Generate a descriptor vector for each descriptor in a metric space in which each component corresponds to the value of the descriptor for each patient;

v. Quantify for each descriptor a first proximity factor between the values of the components of the first characteristic vector and the values of the components of the descriptor vector;

vi. Select and include in the subset at least one descriptor having optimal quantified proximity factor values;

vii. Quantify:

a second proximity factor between the values of the components of each descriptor not selected during the first selection step and the values of the components of the descriptor vector(s) selected during the first selection step; and a third proximity factor between the values of the components of each descriptor not selected during the first selection step and the values of components of the characteristic vector;

viii. Selecting and including in the subset at least one new descriptor as a function of the value of the second proximity factor and the value of the third proximity factor quantified during the second step of quantification.

One advantage of the invention is to propose a device for selecting a subset of different electrophysiological descriptors to characterize a cardiac activity. The selection device according to the invention makes it possible to select a subset of electrophysiological descriptors that is relevant to discriminate between two different populations, from a set of physiological descriptors. Thus, it is possible to select from a large number of descriptors that take into account different signal types, different signal markers and various statistical modalities for calculation, a relevant subset of descriptors. Furthermore, as the device according to the invention takes into account the third proximity factor, a set of electrophysiological descriptors that are not redundant with each other to characterize said cardiac activity is then obtained. The selection device according to the invention thus makes it possible to obtain an effective and non-redundant subset for the discrimination of two populations.

According to one embodiment, the electrodes are arranged on the surface of the patient using adhesive strips. This characteristic is a practical way of implementation to lay out the electrodes on the patient.

According to one embodiment, the device comprises a device for detecting a patient's breathing phases, preferably a plethysmography belt. This provision makes it possible to carry out measurements during a breathing phase of the patient that does not disturb said measurements.

According to one embodiment, the device according to the invention is capable of implementing the method according to the invention.

BRIEF DESCRIPTION OF THE FIGURES

Other characteristics and advantages of the invention will become clearer upon reading the following detailed description, in reference to the appended figures, that illustrate.

DESCRIPTION OF THE INVENTION

According to a first aspect, the invention relates to a method for selecting a subset of electrophysiological descriptors characteristic of a characteristic cardiac activity.

The invention also relates to a device for selecting a subset of electrophysiological descriptors characteristic of a characteristic cardiac activity. The device according to the invention is capable of implementing the invention mentioned above. Subsequently, the elements described in this description will be applicable both to the method according to the invention and to the device according to the invention.

Figure 1:
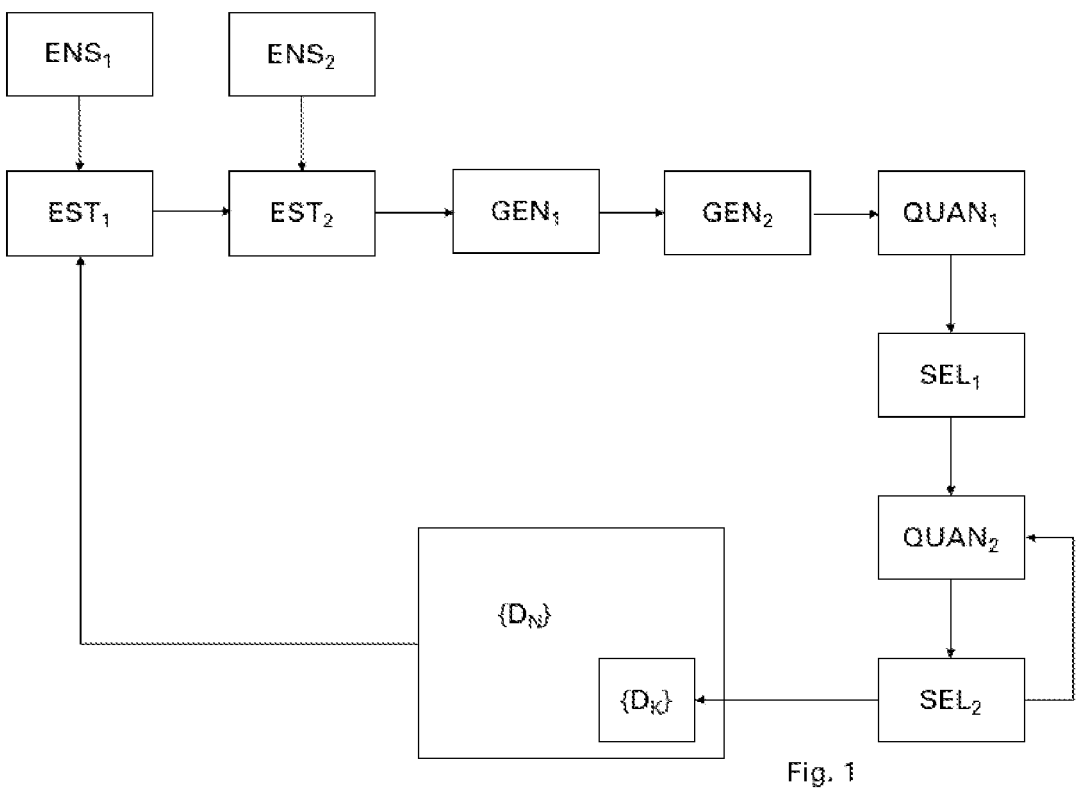
FIG. 1: a schematic flowchart of the method according to the invention.

The method according to the invention will be described in support of FIG. 1, which is a schematic flowchart of the method according to the invention.

According to a first aspect, the invention relates to a method for selecting a subset $\{D_k\}$ of first electrophysiological descriptors $D_i$ characteristic of an electrical activity representative of a characteristic cardiac activity. "Characteristic cardiac activity" is taken to mean a patient's cardiac activity which may be characteristic of said patient's condition.

The subset $\{D_k\}$ of first electrophysiological descriptors $D_i$ is selected from a set $\{D_N\}$ of electrophysiological descriptors. Thus, the method according to the invention relates to the selection, from a set $\{D_N\}$ of electrophysiological descriptors, of a subset $\{D_k\}$ of more restricted descriptors. The aim of the method according to the invention is to perform a relevant and reduced selection of several descriptors $D_i$ from the set $\{D_N\}$.

"Electrophysiological descriptor $D_i$" is taken to mean a context of measurement of an electrical datum associated with an activity detected on the surface of a patient. Each first electrophysiological descriptor $D_i$ is associated with the recording of at least one channel $V_i$. The recording of a channel $V_i$ corresponds to the recording of the electrical activity captured by at least one electrode EL arranged on the surface of a patient's body. For the purposes of the recordings, the invention may be implemented notably by means of a memory making it possible to record the data acquired and/or the data processed by one of the steps of the method according to the invention. Each first descriptor $D_i$ is associated with at least one channel $V_i$ on a predefined area $Z_i$ on the patient's body. "Predefined area $Z_i$" is taken to mean the area of the patient's body on which are deposited the measuring electrode(s) EL, the electrical activities of which are recorded to obtain the channel(s) $V_i$. Thus, the surface of a patient's body may be segmented into different functional and/or geometrical and/or physiological areas. These areas may therefore correspond to geographical areas on the patient's body, to functional areas in relation to the patient's cardiac activity, or to areas corresponding to the patient's physiology and/or physiology.

Each first descriptor $D_i$ is associated with a signal type $T_i$ measured on the selected channels $V_i$. For example, signal type $T_i$ is taken to mean the measurement of a tension between two electrodes. The different types of signals $T_i$ that can be selected will be described later.

Each first descriptor $D_i$ is associated with a signal marker $M_i$. "Signal marker $M_i$" is taken to mean the characteristic of the signal type $T_i$ that will be measured. According to examples of used signal markers $M_i$, certain comprise the measurement of frequency and energy characteristics of the signal. According to other examples, markers may comprise electrical voltage or tension measurement. The different signal markers $M_i$ that may be selected are described below.

Each first descriptor $D_i$ is associated with a statistical modality $MS_i$. "Statistical modality $MS_i$" is taken to mean a statistical measurement modality applied to the measurements made on the signals. For example, a statistical modality $MS_i$ may be the calculation of the average of the signal marker $M_i$ measured on several electrodes. The different statistical modalities $MS_i$ that may be selected will be described later.

Each first electrophysiological descriptor $D_i$ is therefore defined by both a selection of the predefined area $Z_i$ of the patient's body, the signal type $T_i$, the signal marker $M_i$ and the statistical modality $MS_i$.

According to one embodiment, at least two first descriptors $D_i$, $D_j$ of the subset $\{D_k\}$ are associated with a different statistical modality $MS_i$. In other words, two of the first descriptors $D_i$, $D_j$ are not associated with the same statistical modality $MS_i$.

According to one embodiment, at least two first descriptors $D_i$, $D_j$ of the subset $\{D_k\}$ are associated with a different signal marker $M_i$. In other words, two of the first descriptors $D_i$, $D_j$ are not associated with the same signal marker $M_i$.

A first step of the method according to the invention corresponds to an estimation $EST_1$, for a first set of patients $ENS_1$, of values of each first electrophysiological descriptor $D_i$. The first set of patients only comprises patients not having a predefined condition $ET_1$. A predefined condition is a condition presenting particular characteristics at the cardiac level, regardless of whether the condition is pathological or not. According to one embodiment, the predefined condition $ET_1$ is a structural heart pathology. The estimation of the values of the first descriptors $D_i$ is performed for each first electrophysiological descriptor $D_i$ of the set of descriptors $\{D_N\}$.

A second step of the method according to the invention corresponds to an estimation $EST_2$, for a second set of patients $ENS_2$, of values of each first electrophysiological descriptor $D_i$. The second set of patients only comprises patients with the predefined condition $ET_1$. The estimation of the values of the first descriptors $D_i$ is performed for each first electrophysiological descriptor $D_i$ of the set of descriptors $\{D_N\}$.

A next step is the generation $GEN_1$ of a first characteristic vector $V_1$ of the condition of each patient. This vector $V_1$ comprises one component per patient of the first set $ENS_1$ and one component per patient of the second set $ENS_2$. Each component of the characteristic vector $V_1$ corresponds to a condition relative to the predefined condition $ET_1$. According to one embodiment, the first vector comprises a first predefined value $vp_1$ for each patient of the first set $ENS_1$. Similarly, the first characteristic vector $V_1$ comprises a second predefined value $vp_2$ for each patient of the second set $ENS_2$. This provision makes it possible to have a characteristic vector $V_1$ which is representative of the condition of patients of the first and second sets $ENS_1$, $ENS_2$. According to an alternative, the components of the first characteristic vector $V_1$ are a function of the level of suffering from the predefined condition $ET_1$ of patients of the first and second sets $ENS_1$, $ENS_2$. According to this provision, the components of the first vector $V_1$ may, for example, have a low value when the patient is hardly affected by the predefined condition $ET_1$ and a high value when the patient is strongly affected by the predefined condition $ET_1$. According to one embodiment, the first characteristic vector $V_1$ comprises a component equal to "zero" for each patient of the first set $ENS_1$. According to one embodiment, the first characteristic vector $V_i$ comprises a component equal to "one" for each patient of the second set $ENS_2$.

A next step of the method according to the invention is the generation $GEN_2$ of a descriptor vector $V_d$ for each first electrophysiological descriptor $D_i$. This generation $GEN_2$ is performed in a metric space. Each component of the descriptor vector $V_d$ corresponds to the value of said first electrophysiological descriptor $D_i$. Thus, each descriptor vector $V_d$ comprises one component per patient of the first and second sets $ENS_1$, $ENS_2$.

A next step of the method according to the invention relates to the first quantification $QUAN_1$ for each descriptor $D_i$ of a first proximity factor between the values of the components of the first characteristic vector $V_1$ and the values of the components of the descriptor vector $V_d$. This step makes it possible to estimate whether a correlation relationship exists between the values of the first characteristic vector $V_1$ and the values of the descriptor vector $V_d$ for each descriptor $D_i$ considered.

According to one embodiment, the first quantification step $QUAN_1$ is carried out by quantifying for each descriptor $D_i$ the statistical correlation between the values of the components of the first characteristic vector $V_1$ and the values of the components of the descriptor vector $V_d$. Alternatively, this quantification may be performed by calculating a quadratic error.

According to one embodiment, the first quantification step $QUAN_1$ is performed using a method for selecting variables such as the LASSO method. Alternatively, a RIDGE regression may be used.

A next step of the method according to the invention is a first selection $SEL_1$ of at least one descriptor $D_i$. In this step, at least one descriptor $D_i$ is selected as a function of the previously quantified values of the first proximity factor of each descriptor $D_i$. The first descriptor(s) $D_i$ selected are included in the subset $\{D_k\}$. The selection is made by taking the descriptor(s) $D_i$ that comprise optimal proximity factor values from all the descriptors $D_i$ of the set $\{D_N\}$. Optimal value is taken to mean a value that reports the proximity of the descriptor vector $V_d$ with the first vector $V_1$. In the event where the proximity factor is a correlation calculation, the optimal value is a maximum value. In a case where the proximity factor is a quadratic error, the optimal value is a minimum value. This step therefore makes it possible to select the descriptor(s) $D_i$ having the greatest proximity with the characteristic vector $V_1$.

A next step in the method is a step of second quantification $QUAN_2$. This step is broken down into two distinct steps. There is firstly the quantification of a second proximity factor between the components of the descriptor vectors $V_d$ of the descriptors $D_i$ that were not selected at the first selection $SEL_1$ and the values of the components of the descriptor vector(s) $V_d$ that were selected at the first selection step $SEL_1$. There is then the quantification of a third proximity factor between the components of the descriptor vectors $V_d$ of the descriptors $D_i$ that were not selected during the first selection $SEL_1$ and the values of the components of the characteristic vector $V_1$. It may be noted that this step of second quantification may be performed from the values of the components of the descriptor vectors $V_d$ and the characteristic vector or from a transformation in metric space of said components.

According to one embodiment, the step of second quantification $QUAN_2$ is carried out by quantifying the statistical correlation between the values of the components of the different vectors involved. Alternatively, this quantification may be performed by calculating a quadratic error.

According to one embodiment, the step of second quantification $QUAN_2$ is performed using a method for selecting variables such as the LASSO method. Alternatively, a RIDGE regression may be used.

A next step of the method according to the invention is a second selection step $SEL_2$ of at least one new descriptor $D_i$ and its inclusion in the subset $\{D_k\}$. The new descriptor $D_i$ is selected as a function of the values of the second proximity factor and the third proximity factor quantified during the second quantification $QUAN_2$. More precisely, during this selection step, the descriptor(s) $D_i$ having a high quantified proximity with the characteristic vector $V_1$ and a low quantified proximity with the descriptor vector(s) $V_d$ previously selected are selected.

Taking into account the first proximity factor, the second proximity factor and the third proximity factor makes it possible to obtain a subset of descriptors $D_i$ which takes into account the redundancy of the information borne by several descriptors $D_i$. According to these characteristics, a classification is obtained which no longer takes into account only the correlation between the descriptor vectors $V_d$ and the first vector $V_1$, but which also makes it possible to select descriptor vectors $V_d$ which have a high correlation value, but are not too similar to the first descriptor vectors $V_d$ selected. This provision makes it possible to select a subset $\{D_k\}$ that comprises non-redundant descriptors $D_i$.

The method according to the invention makes it possible to select a subset $\{D_k\}$ of descriptors $D_i$ which makes it possible to discriminate two sets of patients in an effective and non-redundant manner. The method according to the invention makes it possible to sort among a large number of electrophysiological descriptors $D_i$ to select therefrom a reduced number capable of differentiating patients according to their having or not the predefined condition $ET_1$.

According to one embodiment, the steps of second quantification $QUAN_2$ and second selection $SEL_2$ are reproduced from the descriptors $D_i$ not selected previously until a predefined number of descriptors $D_i$ is obtained. This method follows several iterations of the steps of second quantification $QUAN_2$ and second selection $SEL_2$ and thus makes it possible to obtain a subset $\{D_k\}$ which comprises the desired number of electrophysiological descriptors $D_i$.

According to one embodiment, the step of second quantification $QUAN_2$ comprises a step of projection in a first plane $P_1$ orthogonal to the descriptor vector(s) $V_d$ associated with the last descriptors selected. During this projection step, all the descriptor vectors $V_d$ that were not previously selected in the plane $P_1$ are projected. Similarly, the characteristic vector $V_1$ is projected in the plane $P_1$. This projection step may be assimilated to the step of second quantification $QUAN_2$ of the second proximity factor between the components of the descriptor vectors $V_d$ not previously selected and the descriptor vectors $V_d$ already included in the subset $\{D_k\}$. Indeed, the projection is equivalent to a quantification of the proximity factor, because the projection of a vector in the plane orthogonal to a vector that is very close to it gives a vector which is practically zero. According to this embodiment, the quantification of the third proximity factor is performed from the components of the projected descriptor vectors $V_d$. According to this embodiment, the quantification of the third proximity factor is performed from the components of the characteristic vector $V_1$ which has been projected. This vector orthogonalization method makes it possible to obtain a subset $\{D_k\}$ in which each descriptor is relevant to discriminate between the two sets of patients $ENS_1$, $ENS_2$. The orthogonalization advantageously makes it possible not to select several electrophysiological descriptors $D_i$ which bear information that is redundant with that of the previously selected descriptors $D_i$.

According to one embodiment, the predefined number of selected descriptors $D_i$ is determined by testing the effectiveness of the subset $\{D_k\}$ of descriptors $D_i$ to discriminate the first set $ENS_1$ of patients from the second set $ENS_2$ of patients. In this way, the number of descriptors $D_i$ is searched for, which makes it possible to obtain the best performance for the subset $\{D_k\}$.

According to one embodiment, the predefined number of selected descriptors $D_i$ is determined by testing the effectiveness of a subset of descriptors by first testing the effectiveness of the first selected descriptor $D_i$. Then, the effectiveness of the first two selected descriptors $D_i$ is tested. A number is then incremented in steps of "1", testing the first three, then the first four descriptors. This iteration is continued until a number "n" of tested descriptors is reached. Finally, the predefined number of descriptors $D_i$ for which the discrimination performance of the first set $ENS_1$ of patients and the second set $ENS_2$ of patients is the highest is maintained. Alternatively, it is possible to start directly from a number "n" of descriptors and increment by steps of "1" until obtaining "N" descriptors. For example, the iterative process may be started by testing the effectiveness of a subset $\{D_k\}$ of seven descriptors $D_i$ up to a set of twenty descriptors $D_i$. For example, it may also start with the test with a subset of ten descriptors $D_i$ and end with a subset of thirty descriptors $D_i$.

Electrophysiological Descriptors

As described previously, each first electrophysiological descriptor $D_i$ is associated with at least one channel $V_i$ of a predefined area $Z_i$ of the patient's body, a signal type $T_i$, a signal marker $M_i$, and a statistical modality for calculation $MS_i$. These four elements will be described in detail below. To select a descriptor $D_i$, a selection is made of a predefined area $Z_i$ from a set of predefined areas $Z_i$. A selection is made of a signal type $T_i$ from a set of signal types $T_i$. A selection is made of a signal marker $M_i$ from a set of signal markers $M_i$. A selection is made of a statistical modality $MS_i$ from a set of statistical modalities $MS_i$.

Patient's Body Area

Figure 2:
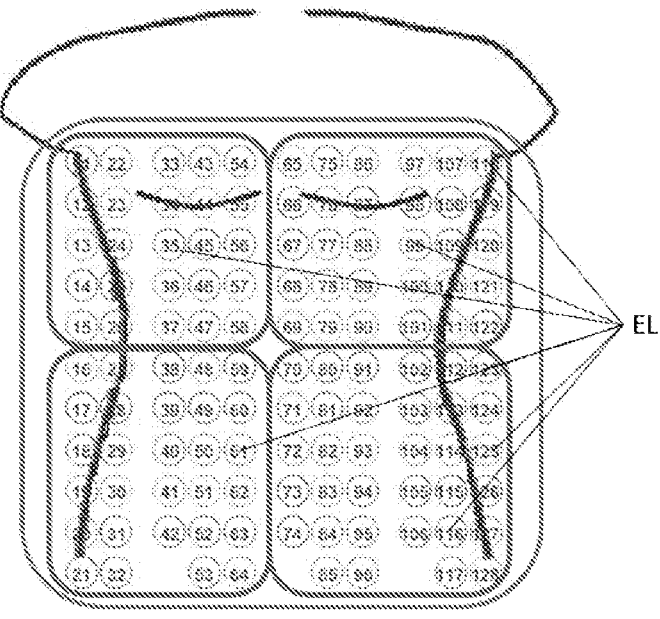
FIG. 2: a front view of the torso of a patient on which is arranged a plurality of measuring electrodes to implement a method according to the invention.

As shown in FIG. 2, a plurality of electrodes EL is deposited on the surface of the torso of each patient of the sets $ENS_1$ and $ENS_2$ to implement the selection method according to the invention. The number of electrodes in the example shown may vary, for example the number of electrodes may be much lower than that shown, or much higher. The plurality of electrodes EL covers a large part of the patient's torso. As can be seen, this plurality of electrodes is separated into four distinct areas on it. A first part of the electrodes EL is located on an upper right area $Z_1$ of the patient's torso. A second part of the electrodes EL is located on an upper left area $Z_2$ of the patient's torso. A third part of the electrodes EL is located on a lower right area $Z_3$ of the patient's torso. A fourth part of the electrodes EL is located on a lower left area $Z_4$ of the patient's torso. Finally, the plurality of electrodes EL is comprised in an area comprising the totality $Z_5$ of the patient's torso.

The demarcation between the areas situated to the left of the torso and those situated to the right of the torso is a vertical line passing through the center of the torso, or substantially through the center of the torso.

The demarcation between the areas situated on the lower torso and those situated on the upper torso is a horizontal line through the center of the torso.

Each area comprises a predefined number of electrodes EL. The number of electrodes arranged per area may be of the order of thirty or so. For example, there may be thirty electrodes EL per area.

Advantageously, each area comprises the same number of electrodes EL. Obviously, the area comprising the entire torso $Z_5$ comprises a different number of electrodes than the others, because this area $Z_5$ comprises the reunion of the electrodes of all the other areas $Z_1$, $Z_2$, $Z_3$ and $Z_4$.

Hereafter, when mention is made of the selection of electrodes in an area, the selection of one or more electrodes EL in said area will be meant.

Alternatively, a lower number of electrodes EL may be provided, for example nine electrodes EL per area $Z_1$, $Z_2$, $Z_3$, and $Z_4$. Thus, in this case, the area $Z_5$ comprising the entire torso of the patient comprises thirty-six electrodes EL.

Each channel $V_i$ is obtained by recording the electrical activity of at least two electrodes EL. These at least two electrodes may be two electrodes from one or more areas of the patient's torso. These at least two electrodes may also be an electrode from an area of the patient's torso and a reference electrode.

Geographical Groups

Figure 3:
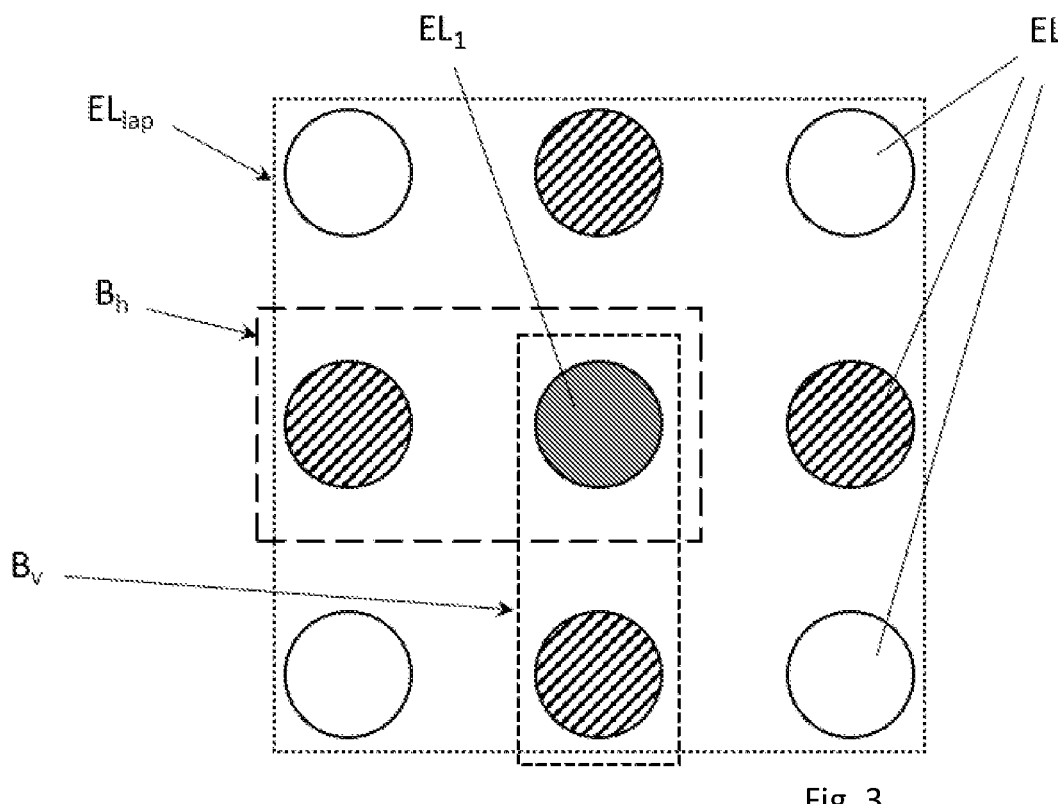
FIG. 3: a view of a plurality of measuring electrodes in a predefined area of the patient's body.

According to one embodiment, the set $\{D_N\}$ comprises at least one second geographical electrophysiological descriptor $D_i$. The at least one geographical descriptor $D_i$ is associated with at least one channel $V_i$ and with several geographical groups. A geographical group is formed by an electrode EL and the four electrodes EL that are situated directly next to it. A geographical group is shown in FIG. 3. This geographical group comprises a central electrode $EL_1$ and the electrode situated directly above it. It also comprises the electrode situated directly below the central electrode $EL_1$, the electrode situated directly to the left of the central electrode $EL_1$, and the electrode situated directly to the right of the central electrode $EL_1$. These four electrodes are shown hatched in FIG. 3. For the second geographical descriptors, the measurement of the value according to the signal type and the signal marker is performed on all the available geographical groups of the plurality of electrodes arranged on the patient's body. Other provisions of electrodes may be envisaged. It is notably possible to select the central electrode and the four electrodes situated at the top left, top right, bottom left and bottom right of the central electrode $EL_1$. These are the electrodes that appear without a pattern in FIG. 3. More electrodes may also be provided, for example nine electrodes in the geographical group. These are the nine electrodes EL in FIG. 3 for example.

For each geographical group, the value obtained for each electrode EL of said group is compared with at least one geographical threshold value. The at least one geographical threshold value is obtained from a statistical distribution of the value of the considered electrode EL of the set of patients $ENS_1$ not having the predefined condition $ET_1$. When at least three electrode values of a geographical group exceed their geographical threshold value, then the geographical group is considered as significant. Finally, the value of the descriptor is the number of significant geographical groups counted. Alternatively, a geographical group may be considered as signifying from two electrodes exceeding their geographical threshold value, or instead with four electrodes.

It may be noted that in the case of a second geographical descriptor, the statistical modality is not taken into account, the value of the descriptor being the number of geographical groups detected.

Advantageously, the subset $\{D_k\}$ of descriptors comprises at least one first descriptor $D_i$ and at least one second geographical descriptor. Additionally, the subset $\{D_k\}$ comprises several first descriptors $D_i$. According to this alternative, the subset $\{D_k\}$ comprises a second geographical descriptor per signal marker used in the first descriptors $D_i$ of the subset $\{D_k\}$.

Signal Type

Each electrophysiological descriptor $D_i$ is associated with a signal type $T_i$. In this section, reference will be made to FIG. 3, which is a schematic representation of nine contiguous electrodes EL on the patient's body. In this figure, each circle represents an electrode EL. The dotted areas represent the different electrodes EL selected in the different signal types.

The signal type $T_i$ may preferably be chosen between four different signal types.

A first signal type $T_i$ is a unipolar signal. A unipolar signal is a signal taken between an electrode EL of the predefined area $Z_i$ and a reference electrode. In other words, the unipolar signal type is the tension measured between the electrode of the predefined area and the reference electrode. "Reference electrode" is taken to mean an electrode that is not situated in one of the areas of the patient's torso defined previously. For example, a reference electrode may be an electrode placed on a lower limb or an upper limb of a patient.

A second signal type $T_i$ is a vertical bipolar signal. A vertical bipolar signal is a signal taken between an electrode in the predefined area and the electrode situated directly below it on the patient's torso. In other words, the signal type acquired is the tension between the two electrodes EL. A vertical bipolar signal is taken between two electrodes of the predefined area $Z_i$. These two electrodes form a vertical bipole $B_v$.

A third signal type $T_i$ is a horizontal bipolar signal. A horizontal bipolar signal is a signal taken between an electrode in the predefined area and an electrode situated directly next to it along a horizontal line on the patient's torso. In other words, the signal type acquired is the tension between the two electrodes EL. The horizontal bipolar signal is taken between two electrodes of the predefined area $Z_i$. These two electrodes form a horizontal bipole $B_h$.

A fourth signal type $T_i$ is a Laplacian signal. A Laplacian signal is estimated by subtracting from the potential of a central electrode $EL_1$ the average of the potentials of the eight electrodes that are directly near said central electrode. In other words, the Laplacian signal is a tension composed between the central electrode $EL_1$ and a set of electrodes EL peripheral to the central electrode $EL_1$. These nine electrodes form a Laplacian electrode $EL_{lap}$.

Signal Markers

Each electrophysiological descriptor $D_i$ is associated with a signal marker $M_i$. A signal marker $M_i$ is a modality of measuring a physical quantity associated with the types of signals measured by the electrodes EL.

The signal marker $M_i$ associated with a descriptor $D_i$ is preferably chosen from fourteen signal markers $M_i$. These signal markers $M_i$ are described below.

A first signal marker $M_i$ corresponds to the measurement of an averaged electrical signal. Averaged electrical signal is taken to mean the calculation, made on the measured tension, of the average between the maximum peak and the minimum peak of the QRS. This measurement of QRS duration is generally quite representative of a cardiac activity.

Two signal markers which are measured on the filtered signal between 40 and 150 Hertz will now be described. The signal is filtered using a bandpass filter. Advantageously, the bandpass filter is a bidirectional Butterworth filter. A bidirectional Butterworth filter has the advantage of limiting oscillations due to filtering, which makes the calculation of values for some signal markers $M_i$ more accurate.

A signal marker $M_i$ on the filtered signal is the QRS duration on the filtered signal. To measure this value, a mark is placed at the start of the QRS and a second mark is placed at the end of the QRS. The time between the two marks is measured. This operation may be performed automatically thanks to a QRS start and end detection algorithm. Alternatively, this time can be measured manually by an operator on an interface. An automatic measurement of the QRS duration and a manual check of said measurement by the operator on the interface may also be provided.

According to one embodiment, the QRS duration is detected by moving a sliding window measuring the energy of the filtered signal. When an energy threshold is exceeded, a mark is placed that marks the start of the window. The QRS end mark is placed in the same way.

Another signal marker $M_i$ is the measurement of the fragmentation of the filtered averaged signal between 40 Hertz and 250 Hertz. According to this marker $M_i$, the number of QRS peaks on the filtered signal is measured. Peak is taken to mean a local maximum of the filtered signal curve. The number of peaks is measured on the section of the curve corresponding to the QRS. The start and end marks of the QRS are set in the same way as for the previous marker $M_i$, which as a reminder is the QRS duration marker on the filtered signal.

The following markers $M_i$ are calculated on the decomposition into wavelets of the signal. For these markers $M_i$, either continuous wavelet decomposition or discrete wavelet decomposition may be used.

The four markers $M_i$ shown below are calculated on the discrete wavelet decomposition.

A first marker $M_i$ is the calculation of the energy on the discrete wavelet decomposition of the signal. Specifically, the energy is calculated on the sum of the coefficients over several levels. Typically, the sum of the coefficients is made between 64 Hertz and 1024 Hertz, i.e. on the four levels of this frequency band. According to one embodiment, the measured energy is normalized with respect to the QRS duration. Alternatively or additionally, the energy is normalized with respect to the maximum signal amplitude.

Figure 5:
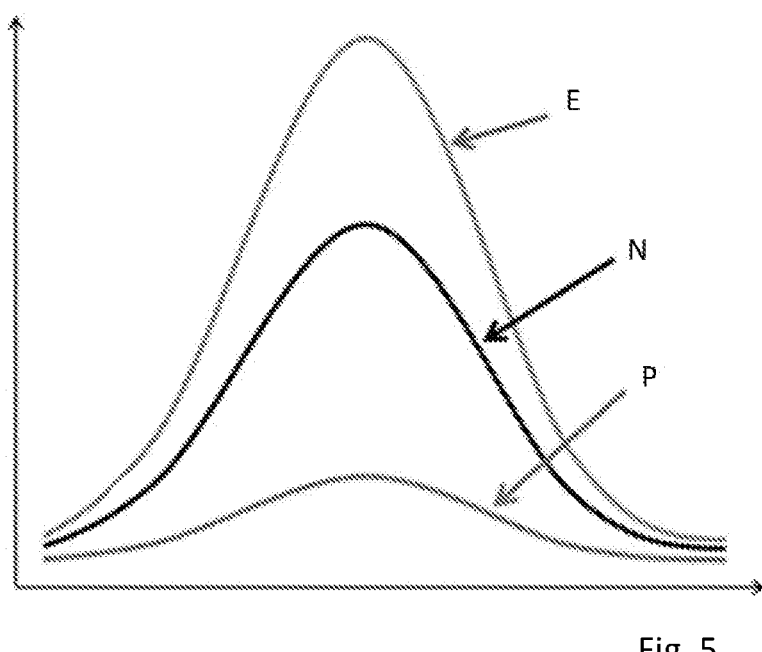
FIG. 5: a graph illustrating the method for calculating a Kurtosis index.

A second marker $M_i$ calculated on the discrete wavelet transform is the measurement of the so-called Kurtosis index $S_{ku}$. "Kurtosis" is taken to mean an index making it possible to estimate the spread of a given curve. FIG. 5 illustrates several measurements of curve spread on three exemplary curves. For a flat curve P, the Kurtosis index is negative. For a slender curve E, the index is positive. Thus, the more the curve is spread, the more negative the Kurtosis. When the curve is narrow, the Kurtosis is positive. The Kurtosis of a curve representing a normal distribution N is equal to zero. Specifically, the Kurtosis $S_{ku}$ is calculated on the sum of the coefficients over several levels of the discrete wavelet decomposition. Typically, the sum of the coefficients is made between 64 Hertz and 1024 Hertz, i.e. on the four levels of this frequency band.

Figure 4:
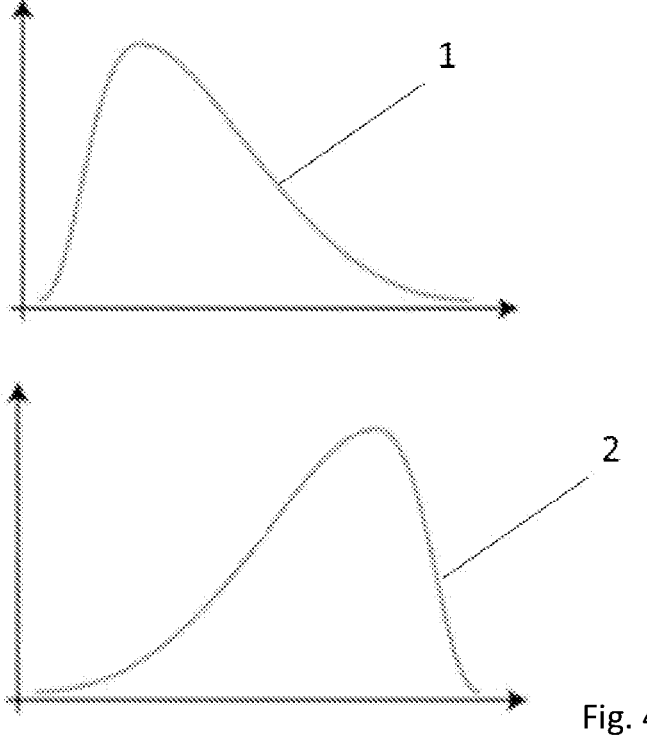
FIG. 4: two curves illustrating the method for calculating an asymmetry index.

A third marker $M_i$ calculated on the discrete wavelet transform is the measurement of the Fischer asymmetry coefficient. This coefficient may also be called "Skewness". This coefficient makes it possible to estimate the asymmetry of a given curve. FIG. 4 illustrates two asymmetry measurements on two curves given as examples. Curve 1 is a curve tending to the left and curve 2 is a curve tending to the right. The Fischer asymmetry coefficient has a positive value when the curve tends to the left. This is the case for curve 1. The Fischer asymmetry coefficient has a negative value when the curve tends to the right. This is the case in FIG. 2. Specifically, the Fischer asymmetry coefficient is calculated on the sum of the coefficients over several levels of the discrete wavelet decomposition. Typically, the sum of the coefficients is made between 64 Hertz and 1024 Hertz, i.e. on the four levels of this frequency band.

A fourth marker $M_i$ calculated on the discrete wavelet transform is the measurement of the number of local minima chains of said decomposition. Specifically, a local minima chain is the presence on several discrete wavelet decomposition levels of a same minimum. By measuring the number of minima that are found in each decomposition level, the number of local minima chains is measured. Typically, the measurement is made between 64 Hertz and 1024 Hertz, i.e. on the four levels of this frequency band. The minima repeating in the 64 Hertz to 128 Hertz bands, then 128 Hertz to 256 Hertz, then 256 Hertz to 512 Hertz and finally 512 Hertz to 1024 Hertz are therefore sought. Alternatively, the measurement of the number of local minima chains may be carried out on the continuous wavelet decomposition.

Another signal marker $M_i$ that may be chosen is the measurement on the continuous wavelet decomposition of the number of local maxima chains. In concrete terms, a local maxima chain is the presence on several discrete wavelet decomposition levels of a same maximum. By measuring the number of maxima that are found in each decomposition level, the number of local maxima chains is measured. Typically, the measurement is made between 64 Hertz and 1024 Hertz, i.e. on the four levels of this frequency band. The maxima repeating in the 64 Hertz to 128 Hertz bands, then 128 Hertz to 256 Hertz, then 256 Hertz to 512 Hertz and finally 512 Hertz to 1024 Hertz are therefore sought. Alternatively, the number of local maxima chains may be measured on the discrete wavelet decomposition.

Figure 6:
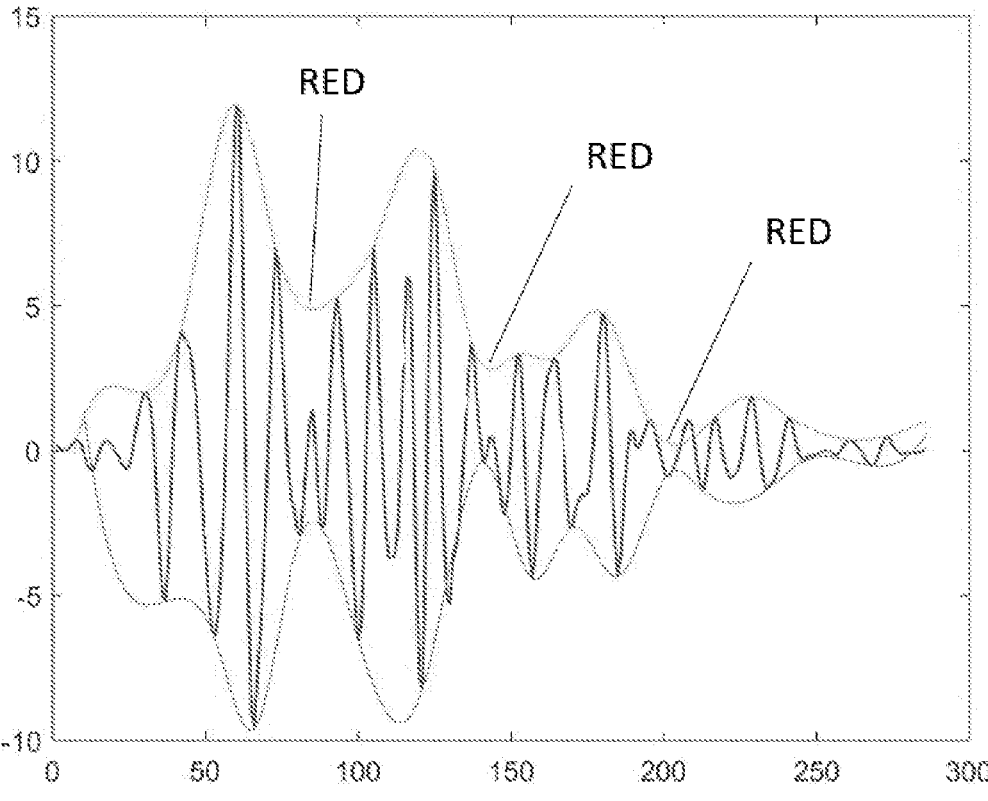
FIG. 6: a view of a curve illustrating the method for calculating the number of areas of reduced amplitude.

The following two signal makers $M_i$ are measured on the wavelet of the signal comprised in the frequency band ranging from 256 Hertz to 512 Hertz of the signal. The first concerns the measurement of the Kurtosis index $S_{ku}$ on this wavelet. "Kurtosis $S_{ku}$" is taken to mean the same indicator as described above in the application. The second signal marker $M_i$ measured on this wavelet is the measurement of the number of reduced amplitude areas RED of the wavelet. To calculate the number of reduced amplitude areas, the upper and lower signal envelopes are created. Thus, the number of areas of reduced amplitude is calculated on the signal envelopes. This is illustrated by FIG. 6 which shows a signal and the reduced amplitude areas RED detected.

The following three signal markers $M_i$ are measured on the wavelet of the signal comprised in the frequency band ranging from 128 Hertz to 256 Hertz of the signal. The first concerns the measurement of the Kurtosis index $S_{ku}$ on this wavelet. Kurtosis $S_{ku}$ is taken to mean the same indicator as that described previously in the application. The second signal marker $M_i$ measured on this wavelet is the measurement of the number of areas of reduced amplitude of the wavelet. The number of areas of reduced amplitude is calculated in the same way as for the marker concerning the wavelet of the signal in the frequency range 256 Hertz to 512 Hertz of the signal. The third signal marker concerns the measurement of the RMS of the wavelet in the frequency band 128 Hertz to 256 Hertz. RMS, or Root Mean Square, is taken to mean the measurement of the effective amplitude of the signal.

Finally, a signal marker $M_i$ that may be selected is measured on the wavelet of the signal comprised in the frequency band ranging from 64 to 128 Hertz. This signal marker $M_i$ relates to the measurement of the RMS (Root Mean Square) effective amplitude of the signal.

Other signal markers $M_i$ may be used beyond the fourteen signal markers $M_i$ described. For example, signal markers $M_i$ may be used which are combinations of signal markers $M_i$ already described.

Statistical Modality

Each first electrophysiological descriptor $D_i$ is associated with a statistical modality $MS_i$. Statistical modality $MS_i$ is taken to mean a modality for processing the different quantities measured in order to calculate a value for each descriptor $D_i$.

It may be recalled that for each first descriptor $D_i$ an area of the body of the patient $Z_i$ is selected, a signal type $T_i$ (therefore the way in which the individual signals of each electrode EL are captured and used), and a signal marker $M_i$. It should be specified that once these three choices have been made, the signal marker $M_i$ for the selected signal type is measured for each electrode of the body area of the patient $Z_i$ available in said selected area $Z_i$. Thus, for each descriptor $D_i$, a plurality of measurements of the value of the signal marker $M_i$ is obtained. Using the statistical modality $MS_i$ makes it possible to transform this plurality of values into a final value for the selected descriptor $D_i$.

For each descriptor $D_i$, a statistical modality $MS_i$ may be selected from a set of available statistical modalities $MS_i$.

A first statistical modality is the fifth percentile minimum of the measured values. It will be recalled that, for the values, all the values measured on each electrode in the predefined area of the body of patient $Z_i$ are taken. For this statistical modality, the five percent of the lowest values are removed from all the measured values and the minimum value is selected from the remaining values. This statistical modality has the advantage, by removing the five percent of the lowest values, of eliminating outliers that could distort the representativeness of the measurement.

A second statistical modality that can be selected is the $95^{th}$ percentile maximum. For this statistical modality, the five percent of the highest values are taken from all the selected values. The highest value of the remaining values is then selected. This statistical modality makes it possible not to take into account, for a measurement of a maximum value, the outliers which could appear in the highest values measured. In this way, there is an upper limit representative of all the measured values.

A third statistical modality $MS_i$ is the average of the measured values. The average is a conventional indicator and representative of a distribution.

A fourth statistical modality $MS_i$ is the standard deviation calculated on the set of measured values. The standard deviation is a representative value of the dispersion of the values. In our case, the dispersion may be a significant value, a large variance in the measurements being able to be the sign of a disorder in the patient's cardiac activity.

A fifth statistical modality $MS_i$ that may be selected is the median. The median value of a set of values is the value making it possible to separate all of the values into two sets of the same size. This value provides a teaching which may vary from that given by the average value, because the median makes it possible not to give too much importance to outliers close to the maximum and minimum of the values measured.

A sixth statistical modality $MS_i$ is the value of the interquartile. To calculate this value, the value of the $25^{th}$ percentile and the value of the $75^{th}$ percentile are calculated. The value of the interquartile represents the difference between the value of the $75^{th}$ percentile and the value of the $25^{th}$ percentile. The interquartile is an interesting statistical value to look at to characterize the distribution of the measured values.

Device for Measuring Descriptor Values

The invention also relates to a device for measuring the values of the electrophysiological descriptors previously described. The invention also relates to the means used to implement the method for selecting a subset of descriptors according to the invention. The characteristics described above concerning the method according to the invention also apply to the device according to the invention. The characteristics described below for the device also apply to the method according to the invention.

The device for measuring the values of electrophysiological descriptors comprises a plurality of electrodes which are arranged on the surface of the patient's body. Each surface electrode defines a channel $V_i$.

According to one embodiment, the device comprises adhesive strips comprising the surface electrodes. According to this aspect, the adhesive strips are intended to be applied to the surface of the patient's body. Advantageously, each adhesive strip comprises several surface electrodes. This provision makes it easier to install the electrodes on the patient, the installation of a strip comprising several electrodes being simpler than installing the electrodes one by one.

According to one aspect, the device comprises a vest or jacket comprising the plurality of measuring electrodes EL. The vest is intended to be put on by the patient. This provision enables a rapid installation of the device on the patient. According to one example, the device comprises at least 14 electrodes.

The device comprises a means of measuring the signal of each channel $V_i$. More precisely, the measurement means is configured to measure an electrical potential of each of the channels $V_i$. For example, the measurement means may be an acquisition card. The acquisition card may comprise an input to collect an electrical signal, and an analog digital converter to digitize the acquired signal. The digitized signal is then transmitted to a calculator. For example, the digitized signal may be transmitted to a computer that performs the processing steps on the signal.

The device comprises a means of calculation. The calculation means records the measurements of channels $V_i$ supplied by the measurement means. The calculator then processes this data.

The calculator calculates the value of each descriptor $D_i$ of the set $\{D_k\}$ for each patient of each set $ENS_1$ and $ENS_2$. This calculation is performed from measurements of channels $V_i$. The calculation is performed according to the predefined area $Z_i$, signal type $T_i$, signal marker $MS_i$ and statistical modality $ST_i$ selected for the descriptor $D_i$ in question.

The calculator then performs the steps of generation $GEN_1$ of the first vector $V_i$ as described previously. It also performs the steps of generation $GEN_2$ of the descriptor vector $V_d$, quantification QUAN of the correlation, first classification $CLAS_1$, second classification $CLAS_2$, and selection SEL described in the method according to the invention. It is able to perform all the other calculation steps described in this application.

According to one embodiment, the device comprises a device for detecting the breathing phases of the patient. Such a device detects when the patient is in the expiration phase or "flat" breathing phase. It also detects when the patient is in the inspiration phase. Breathing tends to interfere with the measurements carried out at the level of the electrodes EL. This is notably the case during inspiration phases during which heart beats and their measurement may be affected. Preferably, the measurement of the potential of each channel $V_i$ is performed during the expiration phase. This provision makes it possible to avoid disturbances caused by a measurement during inhalation phases. The device for detecting breathing phases may be connected to the calculator. Alternatively, it is connected to the means of measuring the signal of each channel $V_i$.

According to one embodiment, the device for detecting breathing phases is a plethysmography belt. The plethysmography belt is a practical way to perform this type of detection.

Nomenclature:

$D_i$: Electrophysiological descriptor $\{D_k\}$: Subset of electrophysiological descriptors $\{D_N\}$: Set of electrophysiological descriptors Inp: Input parameter $V_i$: Channel $Z_i$: Predefined area of the patient's body $Z_1$: Upper right area of the patient's torso $Z_2$: Upper left area of the patient's torso $Z_3$: Lower right area of the patient's torso $Z_4$: Lower left area of the patient's torso $Z_5$: Area covering the totality of the patient's torso $T_i$: Signal type $M_i$: Signal marker $MS_i$: Statistical modality for calculation EL: Electrode $EL_1$: Central electrode $EL_{lap}$: Laplacian electrode $B_v$: Vertical bipole $B_h$: Horizontal bipole DISPO: arrangement of a plurality of electrodes ENR: Recording of a plurality of electrical activities EST: Estimation of descriptors COMP: Comparison of the value of a descriptor with a threshold value $V_{threshold}$: Threshold value CALC: Calculation of a score $S_{ku}$: Kurtosis N: Curve representing a normal distribution P: Flat curve E: Slender curve 1: Curve tending to the left 2: Curve tending to the right RED: Reduced amplitude range

The invention claimed is:

1. A method implemented by computer for selecting a subset of first electrophysiological descriptors characteristic of a characteristic cardiac electrical activity from a set of first predefined descriptors wherein each first electrophysiological descriptor is associated with at least one channel, a signal type, a signal marker and a statistical modality for calculation; at least one first descriptor of the subset being associated with a statistical modality different from that of another first descriptor of the subset and with a signal marker different from that of the other first descriptor; the method comprising recording a plurality of electrical activities defining said channels and:

estimating, for a first set of patients not having a predefined condition, of values of each descriptor of the set of predefined descriptors;

estimating, for a second set of patients having the predefined condition, of values of each descriptor of the set of predefined descriptors;

generating a first vector characteristic of the condition of each patient of the first and second sets of patients in which each component corresponds to a condition relative to the predefined condition;

generating a descriptor vector for each descriptor in a metric space in which each component corresponds to the value of the descriptor for each patient;

first quantifying for each descriptor a first proximity factor between the values of the components of the first characteristic vector and the values of the components of the descriptor vector;

first selection and inclusion in the subset of at least one descriptor having optimal quantified proximity factor values;

second quantifying:

of a second proximity factor between the values of the components of each descriptor not selected during the first selection step and the values of the components of the descriptor vector selected during the first selection step; and of a third proximity factor between the values of the components of each descriptor not selected during the first selection step and the values of the components of the characteristic vector;

second selecting and inclusion in the subset of at least one new descriptor as a function of the value of the second proximity factor and the value of the third proximity factor quantified during the step of second quantification.

2. The method according to claim 1, wherein the steps of second quantification and second selection are reproduced from the descriptors not previously selected until a predefined number of selected descriptors is obtained.

3. The method according to claim 1, wherein the quantification of the first proximity factor and/or the second proximity factor, and/or the third proximity factor is a calculation of the correlation of vectors between them.

4. The method according to claim 1, wherein the step of second quantification comprises a step of projection, in a first plane orthogonal to the descriptor vector associated with the last descriptors selected, of each descriptor vector not selected and of the characteristic vector; wherein the quantification of the third proximity factor and performed from the projected vector projection components; and wherein the second selection is performed as a function of the third proximity factor only.

5. The method according to claim 2 wherein the predefined number of selected descriptors is determined by testing the effectiveness of a set of first n descriptors selected to characterize a given electrical activity, n corresponding to the number of descriptors taken from the selected descriptors, starting from the first to the nth descriptor selected, and incrementing the value of n by steps of 1.

6. The method according to claim 1, wherein the set comprises at least one second geographical descriptor associated with several channels and several geographical groups, each geographical group being formed by a central channel and the at least four channels close to the central channel, the value of the electrophysiological descriptor being determined:

by comparing the value, for each geographical group, of the measurement of each channel according to the signal type and the signal marker selected with at least one geographical threshold value specific to said electrophysiological descriptor and said channel; and by counting the number of geographical groups for which the value of at least three channels exceeds its own geographical threshold value.

7. The method according to claim 1, wherein for each first descriptor, the at least one channel is derived from a predefined area on the body of the patient is chosen between:
an upper right area of the torso;
an upper left area of the torso;
a lower right area of the torso;
a lower left area of the torso; and
an entire torso of the patient.

8. The method according to claim 1, wherein for each descriptor, the signal type analyzed is chosen between:
a unipolar signal taken between an electrode of the chosen body area and a reference electrode;
a vertical bipolar signal taken between two electrodes of the given area, one of the two electrodes being offset along a vertical line with respect to the other electrode;
a horizontal bipolar signal taken between two electrodes of the given area, one of the two electrodes being offset along a horizontal line with respect to the other electrode; and
a Laplacian signal estimated by subtracting from the potential of a central electrode the average tension of the eight electrodes directly adjacent to said central electrode.

9. The method according to claim 1, wherein for at least one descriptor, the signal marker is the measurement of the voltage of an averaged signal.

10. The method according to claim 1, wherein for at least one descriptor, the signal marker is the measurement, on the averaged and filtered signal between 40 and 250 Hertz, of the duration of depolarization of the ventricles or fragmentation of the signal during depolarization of the ventricles.

11. The method according to claim 1, wherein for at least one descriptor, the signal marker is the measurement on the discrete wavelet decomposition of the signal:
of the energy of the sum of the wavelets;
of the Kurtosis;
of the Fisher asymmetry coefficient; or
of the number of local minima.

12. The method according to claim 1, wherein for at least one descriptor, the signal marker is the measurement on the continuous wavelet decomposition of the signal of the number of chains of local maxima.

13. The method according to claim 1, wherein for at least one descriptor, the signal marker is:
either the measurement on the wavelet taken between 256 and 512 Hertz of the signal:
i. of the Kurtosis; or
ii. of the number of areas with reduced amplitudes;
or the measurement on the wavelet taken between 128 and 256 Hertz of the signal:
iii. of the Kurtosis;
iv. of the number of areas of reduced amplitude; or
v. of the RMS (Root Mean Square);
or the measurement on the wavelet taken between 64 and 128 Hertz of the RMS (Root Mean Square).

14. The method according to claim 1, wherein for each first descriptor, the statistical modality is chosen from:
the fifth percentile minimum of the measured values of the signal on each electrode of the predefined area;
the ninety fifth percentile maximum of the measured values of the signal on each electrode of the predefined area;
the average of the measured values of the signal on each electrode of the predefined area;
the standard deviation of the measured values of the signal on each electrode of the predefined area;
the median of the measured values of the signal on each electrode of the predefined area; and
the interquartile of the measured values of the signal on each electrode of the predefined area.

15. A device for selecting a subset of electrophysiological descriptors, the device comprising:
a plurality of surface electrodes configured to be deposited on a patient's body and to measure an electrical potential of the surface of the patient's body, each surface electrode defining a channel;
a means of measuring the signal of each channel;
at least one calculation means configured to:
i. estimate for a first set of patients not having a predefined condition, the values of each electrophysiological descriptor of a set of first predefined descriptors, each first descriptor being associated with at least one channel, a signal type, a signal marker and a statistical modality for calculation; at least one first descriptor of the subset being associated with a statistical modality different from that of another first descriptor of the subset and a signal marker different from that of the other first descriptor;
ii. estimate for a second set of patients having the predefined condition the values of each descriptor of the set of predefined descriptors;
iii. generate a first vector characteristic of the condition of each patient of the first and second sets of patients in which each component corresponds to a condition relative to the predefined condition;
iv. generate a descriptor vector for each descriptor in a metric space in which each component corresponds to the value of the descriptor for each patient;
v. quantify for each descriptor a first proximity factor between the values of the components of the first characteristic vector and the values of the components of the descriptor vector;
vi. select and include in the subset at least one descriptor having optimal quantified proximity factor values;
vii. quantify:
a second proximity factor between the values of the components of each descriptor not selected during the first selection step and the values of the components of the descriptor vector selected during the first selection step; and
a third proximity factor between the values of the components of each descriptor not selected during the first selection step and the values of the components of the characteristic vector;
viii. select and include in the subset at least one new descriptor as a function of the value of the second proximity factor and the value of the third proximity factor quantified during the step of second quantification.

16. A device for selecting a subset of first electrophysiological descriptors characteristic of a characteristic cardiac electrical activity from a set of first predefined descriptors wherein each first electrophysiological descriptor is associated with at least one channel, a signal type, a signal marker and a statistical modality for calculation; at least one first descriptor of the subset being associated with a statistical modality different from that of another first descriptor of the subset and with a signal marker different from that of the other first descriptor, the device comprising a plurality of electrodes, a receiver of the signals measured by the electrodes, a memory for recording measured data including a plurality of electrical activities defining said channels, and a calculator for performing operations and processing on the measured data, said performing operations and processing on the measured data comprising:

estimating, for a first set of patients not having a predefined condition, of values of each descriptor of the set of predefined descriptors;

estimating, for a second set of patients having the predefined condition, of values of each descriptor of the set of predefined descriptors;

generating a first vector characteristic of the condition of each patient of the first and second sets of patients in which each component corresponds to a condition relative to the predefined condition;

generating a descriptor vector for each descriptor in a metric space in which each component corresponds to the value of the descriptor for each patient;

first quantifying for each descriptor a first proximity factor between the values of the components of the first characteristic vector and the values of the components of the descriptor vector;

first selection and inclusion in the subset of at least one descriptor having optimal quantified proximity factor values;

second quantifying:

of a second proximity factor between the values of the components of each descriptor not selected during the first selection step and the values of the components of the descriptor vector selected during the first selection step; and of a third proximity factor between the values of the components of each descriptor not selected during the first selection step and the values of the components of the characteristic vector;

second selecting and inclusion in the subset of at least one new descriptor as a function of the value of the second proximity factor and the value of the third proximity factor quantified during the step of second quantification.

* * * * *